United States Patent
Bierl et al.

(10) Patent No.: US 9,027,386 B2
(45) Date of Patent: May 12, 2015

(54) HYDROGEN SENSOR AND A DETECTION METHOD FOR HYDROGEN CONCENTRATION

(75) Inventors: Rudolf Bierl, Regensburg (DE); Philippe Grass, Regensburg (DE); Stephan Heinrich, Pfeffenhausen (DE); Thorsten Knittel, Regensburg (DE); Andreas Wildgen, Nittendorf (DE)

(73) Assignee: Continental Automotive GmbH, Hannover (DE)

( * ) Notice: Subject to any disclaimer, the term of this patent is extended or adjusted under 35 U.S.C. 154(b) by 561 days.

(21) Appl. No.: 12/956,711

(22) Filed: Nov. 30, 2010

(65) Prior Publication Data

US 2011/0126611 A1 Jun. 2, 2011

(30) Foreign Application Priority Data

Dec. 1, 2009 (DE) .................. 10 2009 056 331

(51) Int. Cl.
*G01N 25/18* (2006.01)
(52) U.S. Cl.
CPC ....................................... *G01N 25/18* (2013.01)
(58) Field of Classification Search
CPC .......................................................... G01N 25/18
USPC .................................. 73/25.01, 25.05, 23.31
See application file for complete search history.

(56) References Cited

U.S. PATENT DOCUMENTS

| | | | |
|---|---|---|---|
| 6,240,777 B1 | 6/2001 | Treutler et al. | |
| 6,361,206 B1 | 3/2002 | Bonne | |
| 7,077,741 B2 * | 7/2006 | Brenner et al. | 454/75 |
| 7,360,392 B2 * | 4/2008 | Konzelmann et al. | 73/1.02 |
| 2003/0154807 A1 | 8/2003 | Hecht et al. | |
| 2007/0289356 A1 | 12/2007 | Konzelmann et al. | |
| 2010/0186482 A1 * | 7/2010 | Bierl et al. | 73/24.06 |

FOREIGN PATENT DOCUMENTS

| | | |
|---|---|---|
| DE | 196 01 791 A1 | 7/1997 |
| DE | 197 44 228 C1 | 11/1998 |
| DE | 101 11 840 A1 | 10/2002 |
| DE | 10 2006 010 901 A1 | 9/2007 |
| DE | 10 2007 033 144 A1 | 1/2009 |

* cited by examiner

*Primary Examiner* — Daniel S Larkin
(74) *Attorney, Agent, or Firm* — Cozen O'Connor

(57) ABSTRACT

A hydrogen sensor includes a support having a first temperature sensor, a heating element and an evaluation unit. The hydrogen sensor furthermore includes a mass flow reduction apparatus by which a gas mass flow over the first temperature sensor and the heating element is reduced. The evaluation unit determines a hydrogen concentration in a gas or gas mixture based on a first temperature detected by the first temperature sensor. A detection method for hydrogen concentration having the hydrogen sensor and a motor vehicle having a fuel cell drive having the hydrogen sensor.

14 Claims, 6 Drawing Sheets

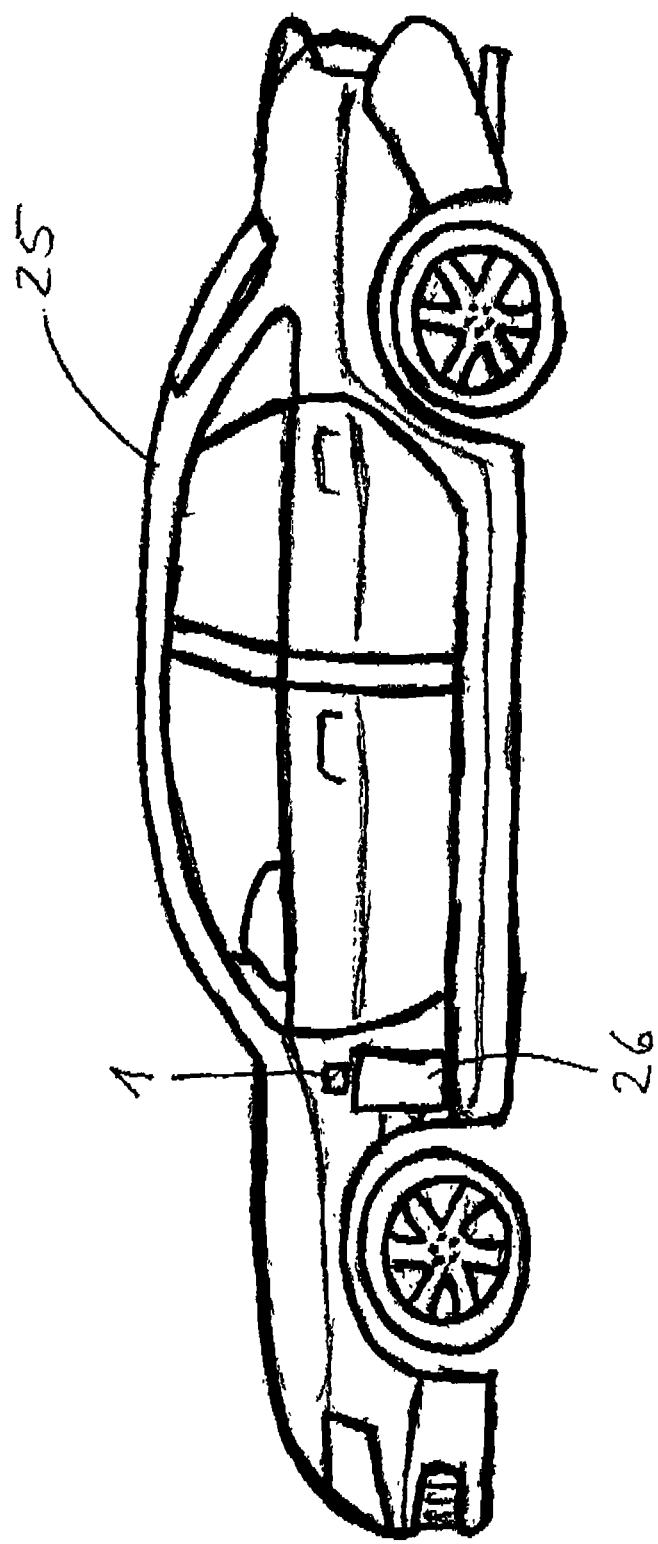

HYDROGEN SENSOR AND A DETECTION METHOD FOR HYDROGEN CONCENTRATION

BACKGROUND OF THE INVENTION

1. Field of the Invention

The present invention relates to a hydrogen sensor, a detection method for hydrogen concentration having the hydrogen sensor, and a motor vehicle having a fuel cell drive having has the hydrogen sensor.

2. Description of the Related Art

Hydrogen sensors normally measure a proportion of hydrogen in a gas or gas mixture using a principle of an electrochemical cell or chemically sensitive layers, for example a Lundstrom FET. These measurement principles are normally suitable for the detection of hydrogen.

One field of use for hydrogen sensors is motor vehicles with fuel cell drives. These motor vehicles require hydrogen sensors because hydrogen is highly flammable. It is therefore necessary to measure the concentration of hydrogen in the vicinity of motor vehicles with fuel cell drives.

Normally, there is a risk of explosion at atmospheric pressure with a proportion of hydrogen by volume of between 4% by volume and 77% by volume. These critical concentrations can occur in the event of a leak from the hydrogen tank or from a hydrogen line. For this reason, hydrogen sensors that monitor the hydrogen content in the surrounding area are an essential component of the safety architecture of a motor vehicle with a fuel cell drive.

One disadvantage of the hydrogen sensors mentioned initially using an electrochemical cell or chemically sensitive layers is that none of these sensors completely satisfy the requirements of the automobile industry in respect of life, measurement range, aging, cross-sensitivity, response time, measurement sensitivity and price.

SUMMARY OF THE INVENTION

An object of the present invention is a hydrogen sensor for automobile use optimized in comparison to the prior art, and to provide a detection method for hydrogen concentration using the hydrogen sensor, as well as to provide a fuel cell vehicle having the hydrogen sensor.

A hydrogen sensor according to one embodiment of the invention comprises: a support on which a first temperature sensor, a heating element arranged adjacent to the first temperature sensor, and an evaluation unit are arranged, and a mass flow reduction apparatus, such that a gas mass flow which flows over the first temperature sensor and the heating element can be reduced, wherein a hydrogen concentration in a gas or gas mixture can be determined by the evaluation unit based on a first temperature detected by the first temperature sensor.

A first temperature sensor, a heating element and an evaluation unit are arranged on a support. The first temperature sensor and the heating element are arranged adjacent to one another. The heating element can heat a gas or gas mixture above the heating element or above the support, while the first temperature sensor can detect a first temperature. The first temperature sensor may have a meandering structure.

The evaluation unit can use the detected first temperature, taking account of the heated heating element, to determine the hydrogen concentration in the gas or gas mixture. By way of example, this can be done based on a family of characteristics stored in the evaluation unit, in particular on a family of hydrogen-concentration/temperature characteristics.

The first temperature sensor and the heating element are arranged on a first side of the support. In this case, the evaluation unit is arranged on a second side of the support, opposite the first side. In particular, the heating element and the first temperature sensor are integrated on a silicon membrane, etched on the rear face, as a support, using a microsystem design (MEMS design).

Furthermore, the hydrogen sensor comprises a mass flow reduction apparatus. The mass flow reduction apparatus can reduce a gas mass flow flowing over the first temperature sensor and the heating element. For example, when the hydrogen sensor is used in a motor vehicle, the hydrogen sensor is not mounted directly in a main line, because of the mass flow reduction apparatus, and, instead, a proportion of the gas mass flow from the main line can be supplied to the hydrogen sensor via the mass flow reduction apparatus. This reduces the gas mass flow flowing over the first temperature sensor and the heating element. Further characteristics of the mass flow reduction apparatus will be explained by describing a detection method for hydrogen concentration.

One advantage of the hydrogen sensor according to one embodiment of the invention is that this hydrogen sensor does not require a chemical reaction with hydrogen, for example on sensitive layers. This simplifies the design of the hydrogen sensor in comparison to the prior art. The hydrogen sensor according to the invention is therefore more cost-effective than hydrogen sensors according to the prior art. A further advantage is a fundamentally different measurement process, since with the temperature, a physical characteristic of the gas is detected, in contrast to the hydrogen sensors according to the prior art, in which hydrogen contained in a gas or gas mixture is determined based on a chemical interaction.

In one advantageous refinement, the mass flow reduction apparatus is a line arranged on the support. As already stated above, the hydrogen sensor can in this way be arranged at a distance from a main gas mass flow, when it is used in a motor vehicle.

In a further advantageous embodiment, the hydrogen sensor has a second temperature sensor arranged on the support. The second temperature sensor is arranged on the support such that the heating element is arranged between the first and the second temperature sensors. The second temperature sensor may likewise have a meandering structure, in the same way as the first temperature sensor.

The use of a second temperature sensor allows a second temperature to be detected, thus improving the accuracy of the hydrogen sensor. The first and second temperature sensors as well as the heating element are, in particular, arranged such that, when a gas or gas mixture flows over the hydrogen sensor, one of the temperature sensors is arranged before the heating element in the flow direction of the gas or gas mixture, and the other temperature sensor is arranged after the heating element in the flow direction.

In one preferred embodiment, the line arranged on the support is arranged around both the first and the second temperature sensors, and around the heating element. This ensures that a reduced gas mass flow can flow over all three elements.

It is also particularly advantageous for the mass flow reduction apparatus to be in the form of a bypass line or blind hole, which passes a proportion of a gas mass flow of a main line to the hydrogen sensor. In particular, the proportion of the gas mass flow which is supplied to the hydrogen sensor via the mass flow reduction apparatus is not greater than 2 kg/h. A mass flowmeter can also be arranged adjacent to the mass flow reduction apparatus to check this mass flow.

A detection method for hydrogen concentration has the following steps: providing of a hydrogen sensor, in particular of a hydrogen sensor according to the invention, comprising: a support on which a first temperature sensor, a heating element arranged adjacent to the first temperature sensor, and an evaluation unit are arranged, and a mass flow reduction apparatus, such that a gas mass flow, which flows over the first temperature sensor and the heating element, can be reduced, a gas or gas mixture flowing over the hydrogen sensor, wherein a reduced gas mass flow of the gas or gas mixture flows over the sensor, and heating of the heating element, detection and transmission of a first temperature by the first temperature sensor to the evaluation unit, determination of a hydrogen concentration based on the detected and transmitted first temperature, taking account of the heated heating element.

A detection method for hydrogen concentration uses the hydrogen sensor according to the invention as described initially. A gas or gas mixture flows over the hydrogen sensor. A gas mass flow which has been reduced by the mass flow reduction apparatus flows over the sensor. For example, the mass flow reduction apparatus passes a proportion of a gas mass flow of a main line to the hydrogen sensor. In particular, the proportion of the gas mass flow passed to the hydrogen sensor is ≤2 kg/h.

The heating element is heated while the flow is passing over the hydrogen sensor. The heating element heats both the gas mass flow and the support, at least partially. In particular, heat is conducted from the heating element to the first temperature sensor. To assist this heat conduction, the carrier has a material with thermally conductive characteristics, such as silicon. The support may also comprise a silicon membrane. In particular, the gas mass flow is heated by free convection.

The first temperature sensor detects a first temperature and transmits this to an evaluation unit of the hydrogen sensor. As described above, the detected first temperature comprises a thermal conduction component and a convection component.

The hydrogen concentration in the gas or gas mixture is determined in the evaluation unit by the detected and transmitted first temperature and taking account of the heated heating element. For example, the hydrogen concentration is determined from a family of characteristics, in particular from a family of hydrogen-concentration/temperature characteristics.

The advantages mentioned above with respect to the hydrogen sensor according to the invention can be achieved by the detection method according to the invention. In particular there is no need for any chemical reaction with hydrogen on the sensor surface in order to determine a hydrogen concentration.

In one advantageous embodiment, the detection method further comprises: comparing the determined hydrogen concentration with a predetermined hydrogen concentration limit value, and outputting a warning signal if the predetermined hydrogen concentration limit value is exceeded. The hydrogen sensor is used in a motor vehicle, as stated above. The detection method can be embodied in a control unit in the motor vehicle. If a predetermined hydrogen concentration limit value is exceeded, the detection method may indicate to a driver of the motor vehicle that the hydrogen concentration limit value has been exceeded. Additionally or alternatively, a control unit in the motor vehicle can ensure that the windows of a passenger compartment of the motor vehicle are opened based on the warning signal.

It is particularly advantageous for the hydrogen concentration limit value to be 2% by volume. As explained initially, the explosion limits for hydrogen are between a concentration of 4% by volume and 77% by volume at atmospheric pressure. A hydrogen concentration limit value of 2% by volume therefore offers a sufficient margin from the explosion limit value of 4% by volume.

In a further advantageous embodiment, the method further comprises: detecting and transmitting a second temperature by a second temperature sensor, arranged on the support, to the evaluation unit. The hydrogen concentration is then advantageously determined by a sum of the detected first and second temperatures. This makes it possible to improve the measurement accuracy of the hydrogen sensor, in comparison to the use of a single temperature sensor.

A motor vehicle having a fuel cell drive has a hydrogen sensor according to the invention. This results in the motor vehicle having the advantages described with respect to the hydrogen sensor. In particular, the hydrogen sensor in the motor vehicle operates using the detection method described above, with the detection method being carried out in a control unit in the motor vehicle.

The hydrogen sensor is preferably arranged in an engine compartment, a passenger compartment, in the vicinity of a tank or in an exhaust gas apparatus of the motor vehicle. The hydrogen sensor is in each case arranged with the use of a mass flow reduction apparatus, in such a way that the hydrogen sensor is arranged in an area in which the flow is calmed. In particular, the mass flow is ≤2 kg/h. The hydrogen sensor is advantageously arranged on a bypass line, a blind hole or in an area in which the flow is calmed.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

One preferred embodiment will be described in detail in the following text with reference to the drawings, in which:

FIG. 6 is a diagram showing the fuel cell drive and the hydrogen sensor with reference to a vehicle.

DETAILED DESCRIPTION OF THE PRESENTLY PREFERRED EMBODIMENTS

A hydrogen sensor according to one embodiment of the invention is used in a motor vehicle with a fuel cell drive. The hydrogen sensor is arranged in one or more of an engine compartment, a passenger compartment, in the vicinity of a tank or adjacent to an exhaust gas apparatus in the motor vehicle. The hydrogen sensor may be connected to a control unit in the motor vehicle. In particular, the hydrogen sensor is arranged on a bypass line, a blind hole or in an area of the motor vehicle in which the flow is calmed.

Figure 1:
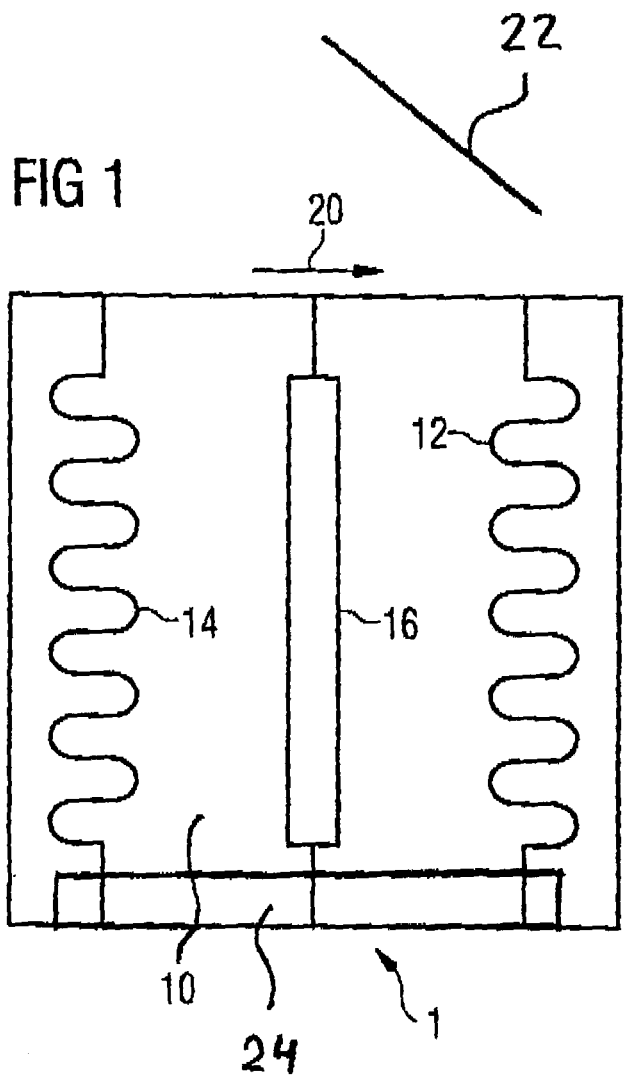
FIG. 1 is a schematic illustration of a hydrogen sensor according to one embodiment of the invention.

FIG. 1 shows a hydrogen sensor 1 according to the invention. The hydrogen sensor 1 has a silicon membrane as the support 10. A first temperature sensor 12 and a second temperature sensor 14 are arranged on the support 10. A heating element 16 is located between the two temperature sensors 12, 14. The temperatures sensors may have a meandering shape. The second temperature sensor 14 is located before the heating element 16 in the flow direction 20 of a gas or gas mixture, while the first temperature sensor 12 is arranged after the heating element 16 in the flow direction 20.

Furthermore, the hydrogen sensor has a mass flow reduction apparatus 22, illustrated schematically in FIG. 1. The mass flow reduction apparatus 22 can reduce the gas mass flow flowing over the temperature sensors 12, 14 and the heating element 16. In particular, the gas mass flow can be reduced to a mass flow of 2 kg/h. By way of example, the hydrogen sensor 1 is attached via the mass flow reduction apparatus to a main line, in which case only a proportion of the main gas mass flow is supplied through the mass flow reduction apparatus to the hydrogen sensor. The mass flow reduction apparatus is, for example, a line which is arranged on the support 10. By way of example, the line may be a bypass line, or may be in the form of a blind hole.

Figure 2:
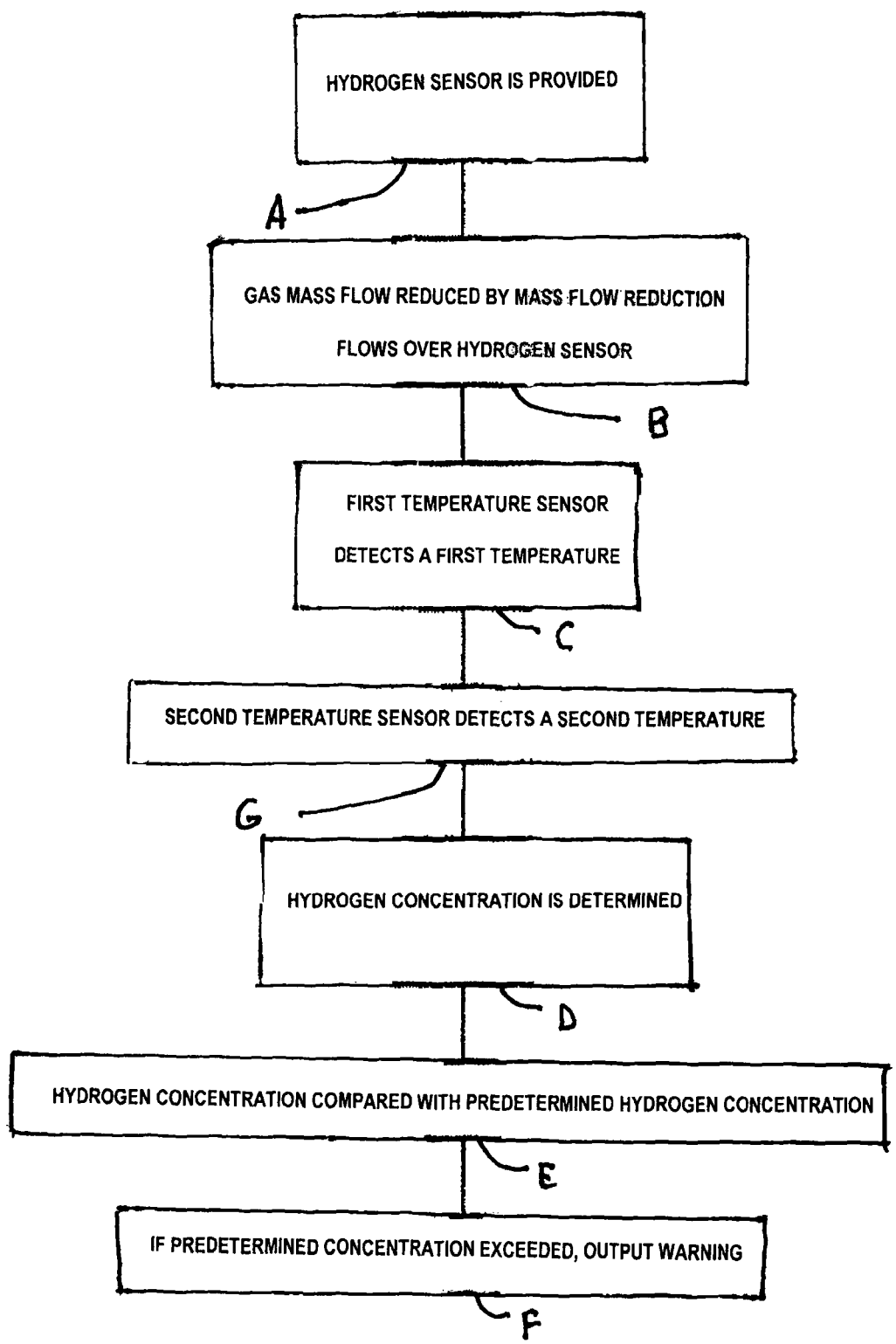
FIG. 2 is a flowchart for a detection method according to one embodiment of the invention.

The detection method will be explained with reference to FIG. 2. In a step A, the hydrogen sensor is provided, in particular the hydrogen sensor 1 according to the invention.

In a step B, the gas mass flow that has been reduced by the mass flow reduction apparatus flows over the hydrogen sensor 1. In this case, the gas mass flow is, in particular, ≤2 kg/h. In order to check the gas mass flow in the mass flow reduction apparatus, said mass flow reduction apparatus may, for example, have a mass flowmeter.

Furthermore, the heating element 16 is heated in step B. The heating element 16 heats the gas flow above the hydrogen sensor 1. The support 10 is also heated via the heating element 16.

in a step C, the first temperature sensor 12 detects a first temperature, and the second temperature sensor 14 detects a second temperature in a step G. The detected temperatures are transmitted to an evaluation unit 24.

In a step D, the hydrogen concentration in the gas mixture is determined using the detected and transmitted temperature taking account of the heated heating element. This is done, in particular, in the evaluation unit 24 based on a sum of the first and second detected temperatures.

The measurement principle of the hydrogen sensor 1 will be explained in the following text with reference to FIGS. 3 to 5. The measurement principle of the hydrogen sensor 1 is based, in particular, on superimposed heat transport between the temperature sensors 12, 14 and the heating element 16. The temperature detected by the temperature sensors 12, 14 comprises a thermal conduction component and a convection component. Thermal conduction takes place between the heating element 16 and the temperature sensors 12, 14. Convection takes place between the heating element 16 and a surface of the hydrogen sensor 1 facing the gas or gas mixture. Free convection is preferably achieved by means of the mass flow reduction apparatus. One characteristic variable for heat transfer on a boundary surface is the heat transfer coefficient.

The heat transfer coefficient can be calculated using the following formula:

$$\alpha = \frac{\lambda}{L} \cdot 0.766 \cdot \left[ \frac{g \cdot L^3 \cdot \rho^2 \cdot (T_{Upper} - T_{Gas})}{T_{Gas} \cdot \eta^2} \cdot \frac{\eta \cdot c_p}{\lambda} \cdot 0.405 \right]^{0.2}.$$

In this case:
α=heat transfer coefficient
g=acceleration due to the Earth's gravity
L=characteristic length (specific for the design, constant if the design does not change)
ρ=density
$T_{Upper}$=absolute temperature of the heater
$T_{Gas}$=absolute temperature of the gas
η=dynamic viscosity
Cp=isotropy coefficient
λ=thermal conductivity Finally, if the gas-dependent parameters of the heat transfer coefficient are considered, this results in the following simplified formula:

$$\alpha \approx \sqrt[5]{\frac{\lambda^4 \cdot \rho^2 \cdot c_p}{\eta}}.$$

Figure 3:
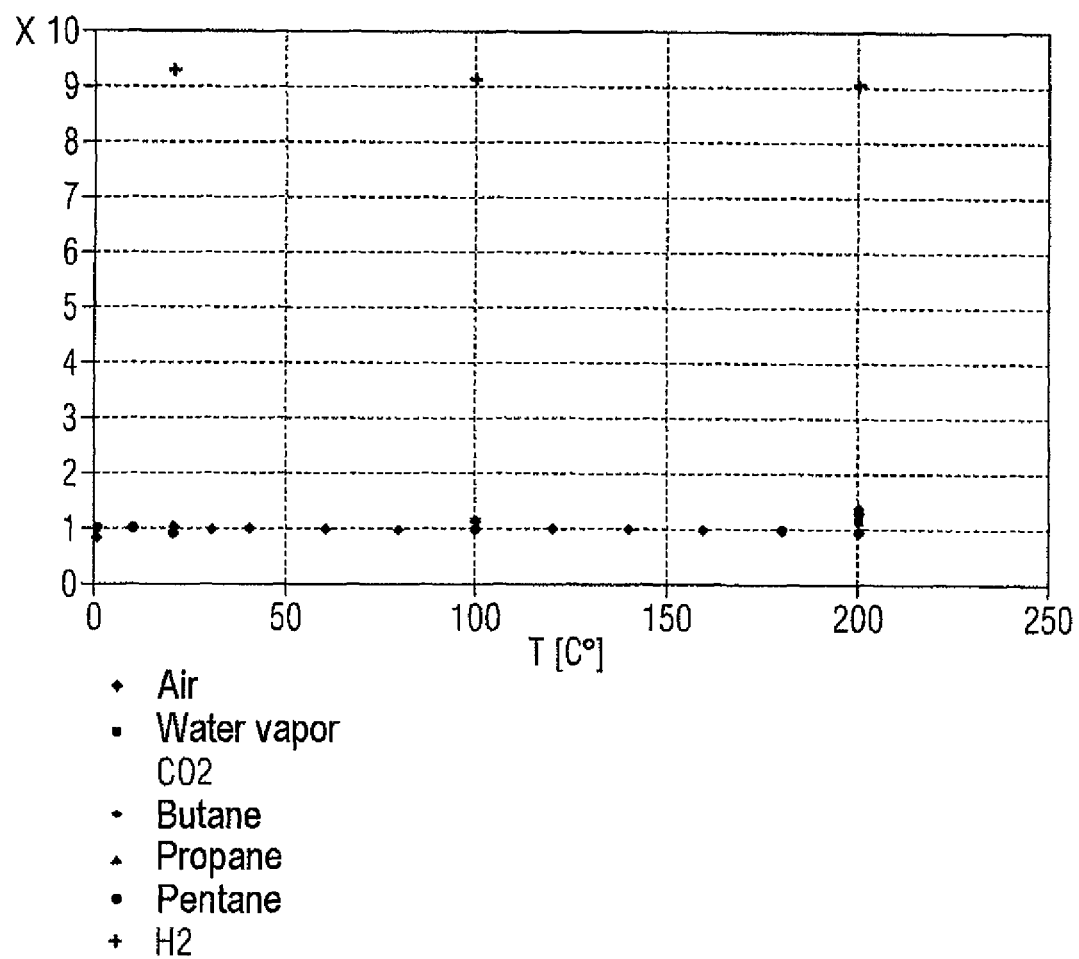
FIG. 3 is a graph of the heat transfer coefficients of hydrogen plotted against the temperature for free convection and normalized with respect to air.

FIG. 3 is a graph of the heat transfer coefficients of the various gases during free convection, plotted against the temperature, using the above formula and normalized with respect to air. Since the illustration is normalized with respect to air, the value X in air is always 1. The value X for hydrogen ($H_2$) varies between X=9 and X=9.5, approximately, depending on the temperature. Hydrogen therefore dissipates heat on the surface of the hydrogen sensor approximately 9 to 9.5 times better than air.

Figure 4:
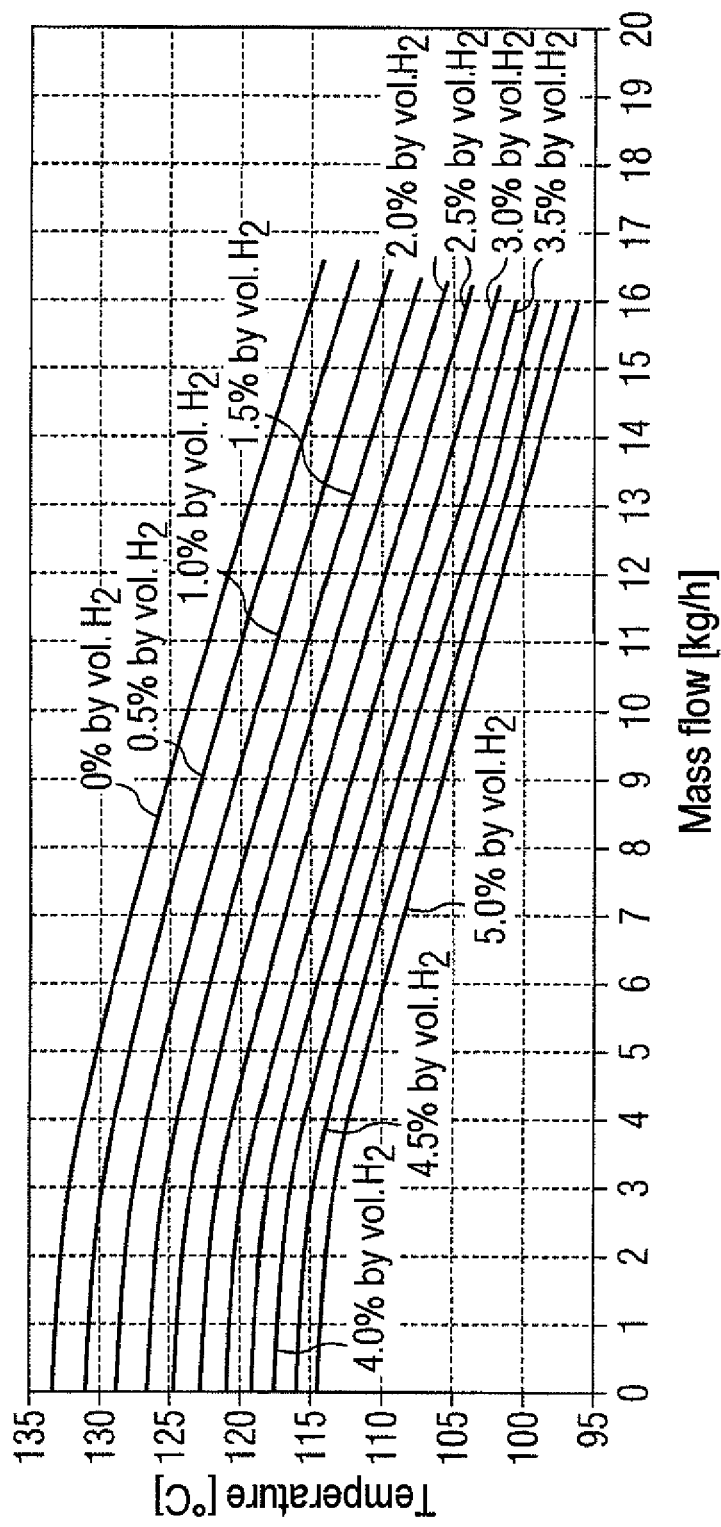
FIG. 4 is a graph of the temperature profiles of different hydrogen concentrations as a function of the mass flow.

FIG. 4 shows temperature profiles for various hydrogen/air mixtures, as a function of the mass flow. The hydrogen/air mixtures vary between 0% by volume of hydrogen to 5% by volume of hydrogen, in each case in 0.5% by volume steps. The temperature corresponds to the sum of the temperatures detected by the two temperature sensors. As can be seen, in particular, from FIG. 4, a plateau is formed in a region up to a mass flow of approximately 2 kg/h, in which the temperature profiles run approximately parallel. This mass flow range is therefore particularly preferable for measurement.

Figure 5:
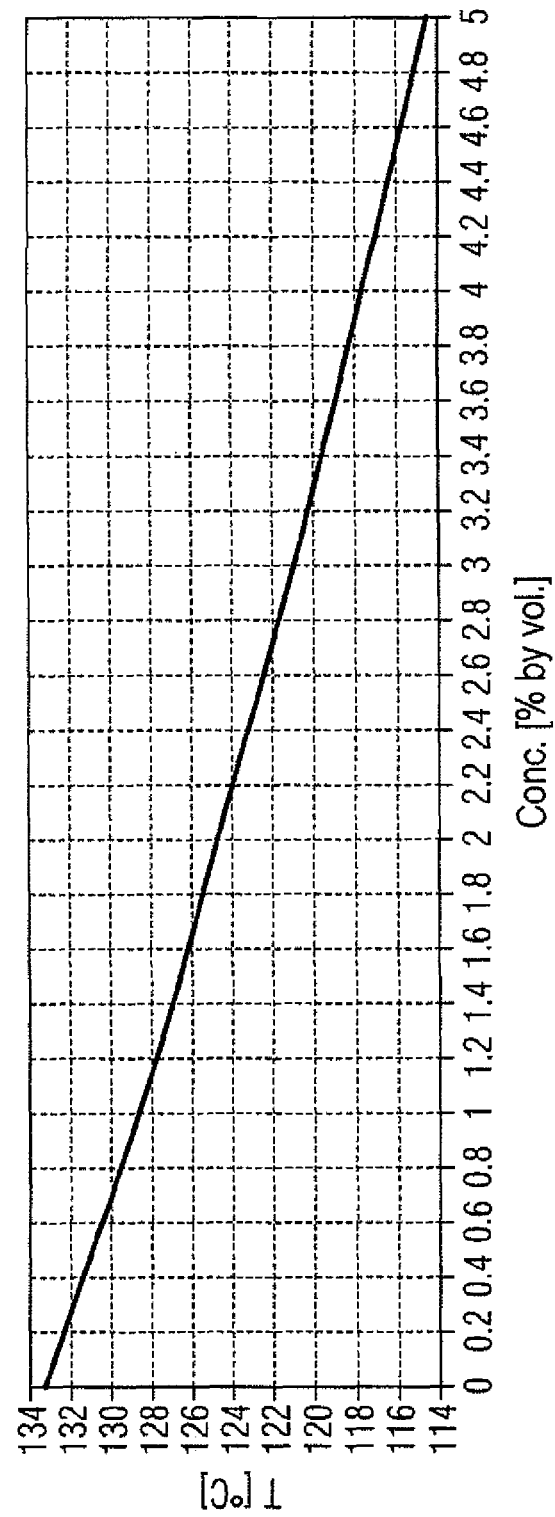
FIG. 5 is a graph of the temperature of the gas or gas mixture as a function of the hydrogen concentration.

FIG. 5 shows a family of hydrogen-concentration/temperature characteristics. This family of characteristics is related to a mass flow of 0 kg/h from FIG. 4 for hydrogen concentrations between 0 and 5% by volume. By way of example, this family of characteristics can be stored in the evaluation unit for the hydrogen sensor 1.

If the temperature detected by the temperature sensors 12, 14 varies during operation of the hydrogen sensor, the sum of the detected temperatures also varies. If the mass flow is constant and the heating power of the heating element is constant, the change in the sum temperature must be due to a change in the composition of the gas or gas mixture, for example an increased or decreased hydrogen concentration. The hydrogen concentration associated with the respective temperature is obtained in a corresponding manner from the family of characteristics.

In a further step E, the evaluation unit compares the determined hydrogen concentration with a predetermined hydrogen concentration. In particular, the predetermined hydrogen concentration is 2% by volume. If the predetermined hydrogen concentration is exceeded, a warning signal is output in a step F, for example to a driver of the motor vehicle. Alternatively or additionally, the output warning signal can be used by a control device in the motor vehicle to open the windows of a passenger compartment.

FIG. 6 is a diagram showing a motor vehicle 25 having a fuel cell drive 26 and a hydrogen sensor 1.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A hydrogen sensor comprising:
a first temperature sensor;
a heating element;
an evaluation unit;
a support having a first side, on which the first temperature sensor and the heating element are arranged adjacent to one another on a silicon membrane, and a second side, on which the evaluation unit is arranged; and
a mass flow reduction apparatus, arranged such that a gas mass flow that flows over the first temperature sensor and the heating element is reduced to less than 2 kg/h,
wherein a hydrogen concentration in a gas or gas mixture is determined by the evaluation unit based at least in part on a first temperature detected by the first temperature sensor.

2. The hydrogen sensor as claimed in claim 1, further comprising:
a second temperature sensor arranged on the support such that the heating element is arranged between the first temperature sensor and the second temperature sensor.

3. The hydrogen sensor as claimed in claim 2, wherein the flow line arranged on the support is arranged around the first temperature sensor, the second temperature sensor, and the heating element.

4. The hydrogen sensor as claimed in claim 1, wherein the mass flow reduction apparatus is one of a bypass line or a blind hole and configured to pass a proportion of a mass flow of a main line to the hydrogen sensor.

5. The hydrogen sensor as claimed in claim 1, wherein a heat transfer coefficient for the sensor is given by:

$$\alpha \approx \sqrt[5]{\frac{\lambda^4 \cdot \rho^2 \cdot c_p}{\eta}},$$

wherein:
$\alpha$=heat transfer coefficient,
$\rho$=density,
$\eta$=dynamic viscosity,
$C_p$=isotropy coefficient, and
$\lambda$=thermal conductivity.

6. A detection method for hydrogen concentration, comprising:
providing a hydrogen sensor, the hydrogen sensor comprising:
a support having a first side, on which a first temperature sensor and a heating element are arranged adjacent to one another on a silicon membrane, and a second side, on which an evaluation unit is arranged; and a mass flow reduction apparatus, such that a gas mass flow which flows over the first temperature sensor and the heating element is reduced;
flowing one of a gas and a gas mixture through the mass flow reduction apparatus to reduce the gas mass flow to less than 2 kg/h
flowing one of the gas and a gas mixture over the hydrogen sensor;
heating by the heating element the gas or gas mixture that flows over the sensor;
detecting and transmitting a first temperature by the first temperature sensor to the evaluation unit; and
determining, by the evaluation unit, a hydrogen concentration based on the detected and transmitted first temperature, taking account of the heated heating element.

7. The detection method as claimed in claim 6, further comprising:
comparing of the determined hydrogen concentration with a predetermined hydrogen concentration limit value; and
outputting of a warning signal if the predetermined hydrogen concentration limit value is exceeded.

8. The detection method as claimed in claim 7, wherein the hydrogen concentration limit value is 2% by volume.

9. The detection method as claimed in claim 6, further comprising:
detecting and transmitting a second temperature to the evaluation unit by a second temperature sensor arranged on the support.

10. The detection method as claimed in claim 9, wherein the determination of the hydrogen concentration is carried out by a sum of the detected first and second temperatures.

11. A motor vehicle comprising:
a fuel cell drive; and
a hydrogen sensor comprising:
a first temperature sensor;
a heating element;
an evaluation unit;
a support having a first side, on which the first temperature sensor and the heating element are arranged adjacent to one another on a silicon membrane, and a second side, on which the evaluation unit is arranged; and
a mass flow reduction apparatus, configured such that a gas mass flow that flows over the first temperature sensor and the heating element is reduced to less than 2 kg/h,
wherein a hydrogen concentration in a gas or gas mixture for the fuel cell drive is determined by the evaluation unit based at least in part on a first temperature detected by the first temperature sensor.

12. The motor vehicle as claimed in claim 11, wherein the hydrogen sensor is arranged in one of an engine compartment, a passenger compartment, a vicinity of a tank, and an exhaust gas apparatus of the motor vehicle.

13. The motor vehicle as claimed in claim 12, wherein the hydrogen sensor is arranged at one of on a bypass line, a blind hole, and in an area in which the flow is calmed.

14. The motor vehicle as claimed in claim 11, wherein the hydrogen sensor is arranged at one of on a bypass line, a blind hole, and in an area in which the flow is calmed.

* * * * *